US012752284B2

(12) United States Patent
Fukuda et al.

(10) Patent No.: US 12,752,284 B2
(45) Date of Patent: Oct. 6, 2026

(54) PARTICLE COLLECTION VESSEL, PARTICLE COLLECTION DEVICE AND PARTICLE COLLECTION METHOD

(71) Applicant: AMANO CORPORATION, Kanagawa (JP)

(72) Inventors: Kyohei Fukuda, Yokohama (JP); Akira Mizuno, Nagoya (JP); Shinjirou Katsushima, Yokohama (JP); Kouichi Kitabayashi, Yokohama (JP); Yuji Makishima, Hamamatsu (JP)

(73) Assignee: AMANO CORPORATION, Kanagawa (JP)

( * ) Notice: Subject to any disclaimer, the term of this patent is extended or adjusted under 35 U.S.C. 154(b) by 687 days.

(21) Appl. No.: 18/245,891

(22) PCT Filed: Sep. 13, 2021

(86) PCT No.: PCT/JP2021/033575
§ 371 (c)(1),
(2) Date: Mar. 18, 2023

(87) PCT Pub. No.: WO2022/065112
PCT Pub. Date: Mar. 31, 2022

(65) Prior Publication Data

US 2023/0356238 A1 Nov. 9, 2023

(30) Foreign Application Priority Data

Sep. 23, 2020 (JP) ................................ 2020-159014

(51) Int. Cl.
*B03C 3/16* (2006.01)
*A61L 9/14* (2006.01)
(Continued)

(52) U.S. Cl.
CPC ................ *B03C 3/16* (2013.01); *A61L 9/145* (2013.01); *A61L 9/16* (2013.01); *B03C 3/363* (2013.01);
(Continued)

(58) Field of Classification Search
CPC ........ A61L 9/145; A61L 9/16; A61L 2209/22; B03C 3/16; B03C 3/363; B03C 3/368;
(Continued)

(56) References Cited

U.S. PATENT DOCUMENTS 4,725,294 A * 2/1988 Berger ................ G01N 1/2202 73/863.22
6,807,874 B2 * 10/2004 Totoki .................... B03C 3/368 73/28.02
(Continued)

FOREIGN PATENT DOCUMENTS

JP H01-180257 A 7/1989
JP 2003-214997 A 7/2003
JP 2004177347 A * 6/2004

OTHER PUBLICATIONS

International Search Report issued in PCT/JP2021/033575; mailed Nov. 9, 2021.

*Primary Examiner* — Jennifer Dieterle
*Assistant Examiner* — Sonji Turner
(74) *Attorney, Agent, or Firm* — Studebaker Brackett PLLC

(57) ABSTRACT

A particle collection vessel (2) which charges particles in air and then collects them includes a vessel body (7) having an opening (8); a suction part (14) provided in the opening (8) and having an inflow path (22) through which the air is flowed from an outside into an inside of the vessel body (7); a discharge part (16) provided in the opening (8) and having an outflow path (26) through which the air is discharged from the inside to the outside of the vessel body (7); a
(Continued)

discharge electrode (15) provided in the inside of the vessel body (7) and to which a high voltage is applied; and a medium storage part (50) provided in the inside of the vessel body (7) and capable of storing a medium for collecting the particles in the air charged by the discharge electrode (15).

20 Claims, 10 Drawing Sheets

(51) Int. Cl.

| | |
|---|---|
| ***A61L 9/16*** | (2006.01) |
| ***B03C 3/36*** | (2006.01) |
| ***B03C 3/38*** | (2006.01) |
| ***B03C 3/41*** | (2006.01) |
| ***B03C 3/53*** | (2006.01) |
| ***G01N 1/22*** | (2006.01) |

(52) U.S. Cl.
CPC .................. *B03C 3/38* (2013.01); *B03C 3/41* (2013.01); *B03C 3/53* (2013.01); *G01N 1/2202* (2013.01); *A61L 2209/22* (2013.01); *B03C 2201/04* (2013.01)

(58) Field of Classification Search
CPC .... B03C 3/38; B03C 3/41; B03C 3/47; B03C 3/53; B03C 3/60; B03C 3/82; B03C 2201/04; B03C 2201/10; C12M 1/28; G01N 1/2202; G01N 1/2247; G01N 1/2273; H01T 19/04
See application file for complete search history.

(56) References Cited

U.S. PATENT DOCUMENTS

| | | | | | |
|---|---|---|---|---|---|
| 6,881,246 | B2 * | 4/2005 | Totoki | B03C 3/011 | 209/127.1 |
| 6,923,848 | B2 * | 8/2005 | Totoki | B03C 3/41 | 95/59 |
| 6,955,075 | B2 * | 10/2005 | Carlson | B03C 3/32 | 73/28.02 |
| 7,041,153 | B2 * | 5/2006 | Totoki | B03C 3/47 | 95/59 |
| 7,156,902 | B1 * | 1/2007 | Altman | B03C 3/15 | 96/96 |
| 7,201,879 | B2 * | 4/2007 | Hill | B03C 3/38 | 250/281 |
| 8,167,986 | B2 * | 5/2012 | Schneider | H01J 37/28 | 96/61 |
| 2003/0136205 | A1 * | 7/2003 | Totoki | G01N 15/0211 | 73/864.71 |
| 2004/0231439 | A1 * | 11/2004 | Totoki | B03C 3/368 | 73/864.71 |
| 2005/0126260 | A1 * | 6/2005 | Totoki | B03C 3/368 | 73/31.02 |
| 2006/0110818 | A1 * | 5/2006 | Hill | G01N 15/06 | 435/287.1 |
| 2007/0034025 | A1 * | 2/2007 | Pant | G01N 1/2202 | 73/864.34 |
| 2011/0000374 | A1 * | 1/2011 | Tanaka | B03C 3/368 | 96/28 |
| 2011/0315011 | A1 * | 12/2011 | Black | G01N 1/2202 | 95/79 |
| 2012/0315666 | A1 * | 12/2012 | Fujioka | G01N 15/0612 | 435/39 |

* cited by examiner

PARTICLE COLLECTION VESSEL, PARTICLE COLLECTION DEVICE AND PARTICLE COLLECTION METHOD

TECHNICAL FIELD

The present invention relates to a particle collection vessel which charges airborne particles and then collects them, a particle collection device provided with the particle collection vessel, and a particle collection method for collecting airborne particles.

BACKGROUND

Traditionally, a collection device is used in pharmaceutical factories, food factories, hospitals and living spaces to check contamination by airborne microbial. For example, as shown in Patent Document 1, a technique is proposed in which a discharge electrode and a dust collection electrode are provided in a collection vessel and airborne particulate substance collected in the collection vessel is deposited on a transparent flat dust collection electrode.

PRIOR ART DOCUMENTS

[Patent Document]

[Patent Document 1] Japanese Patent Laid-Open No. 2003-214997

SUMMARY OF THE INVENTION

Problems to be Solved by the Invention

However, the technique described in the above Patent Document 1 has the following problems.

(1) In Patent Document 1, the collection vessel has three openings including an opening provided in the upper portion, an air inflow port provided in the side portion and a communication port corresponding to a discharge port. Therefore, in order to store and transport the vessel safety after the particles are collected, it is necessary to close all the openings. In addition, there is a problem that because such a collection vessel is not available in the market and it is needed to additionally process the commercial product or to be newly manufactured, the cost increases.

(2) Since the dust collection electrode is not placed on the entire bottom portion of the collection vessel, fine particles may accumulate and adhere to the bottom portion, making it difficult to improve collection performance. In addition, with the arrangement of the inflow port, the discharge electrode and the communication port as shown in Patent Document 1, it is difficult to improve the collection performance because the charged particles may not be collected by the dust collection electrode and flow out directly to the communication port (the discharge port). Furthermore, because the inflow port is disposed on the side surface of the collection vessel, airborne fine particles introduced into the collection vessel do not necessarily pass through the charged area generated by the discharge electrode, making it difficult to improve the charging performance.

(3) Since the collected fine particles are collected on the transparent flat plate (the dust collection electrode that forms a conductive transparent film on the surface of the transparent plate), when the particles collected on the flat plate are used in a post-processing such as a PCR processing, a process to scrape the particles from the flat plate is required, causing a problem that the operation is troublesome.

In view of the above problems, it is an object of the present invention to provide a particle collection vessel, a particle collection device and a particle collection method which have excellent economic efficiency, enable performing the next processing easily after the particles are collect performance.

Means of Solving the Problems

In order to achieve the above purpose, the first particle collection vessel according to the present invention is a particle collection vessel which charges particles in air and then collects them, and includes: a vessel body having an opening; a suction part provided in the opening and having an inflow path through which the air is flowed from an outside into an inside of the vessel body; a discharge part provided in the opening and having an outflow path through which the air is discharged from the inside to the outside of the vessel body; a discharge electrode provided in the inside of the vessel body and to which a high voltage is applied; and a medium storage part provided in the inside of the vessel body and capable of storing a medium for collecting the particles in the air charged by the discharge electrode.

In the second particle collection vessel, the medium is a conductive liquid.

According to the first and second particle collection vessel, since the suction part and the discharge part are provided in the opening of the vessel body, the vessel distributed in the market can be used as it is without processing, which increases the economic efficiency. In addition, since the particles are collected in the medium in the vessel body, the processing (for example, a PCR processing) after the particles are collected can be easily performed, and handling can be easily performed.

In the third particle collection vessel, the suction part includes a conductive cylindrical body whose one end is opened to the outside of the vessel body and whose other end is opened to the inside of the vessel body, and the discharge electrode is provided at the other end of the cylindrical body toward the liquid.

According to the third particle collection vessel, the air sucked into the vessel body is guided near the liquid surface and caused to be collided with the liquid surface so that the particles in the air can be brought into contact with and mixed with the liquid. As a result, the particle collection efficiency can be improved. In addition, since the discharge electrode is provided in the conductive cylindrical body, the mechanism of power supplying (application of a high voltage) can be facilitated.

According to the fourth particle collection vessel, an opening area of the other end of the suction part is set smaller than an opening area of one end of the suction part.

According to the fourth particle collection vessel of the present invention, since the velocity at which the air flowing into the inside from the suction part is collied with the liquid surface increases, the degree of contact and mixing of the particles with the liquid increases, and the collection efficiency of particles can be improved.

According to the fifth particle collection vessel of the present invention, the discharge electrode is formed of a wire electrode having a bundle of fibers.

According to the fifth particle collection vessel of the present invention, the wire electrode can generate a charged area at a lower voltage compared to a needle electrode, so that it can be operated by, for example, a battery having an excellent portability. In addition, since the discharge electrode is formed of a wire electrode having a bundle of fibers, dirt is hard to adhere to the electrode, and even if a discharging wire electrode becomes unable to discharge due to dirt, for example, another wire electrode starts discharging by alternating action, so that an excellent durability can be achieved.

In the sixth particle collection vessel of the present invention, the discharge electrodes are arranged at equal intervals along a circumferential direction of the suction part, and a tip portion of each discharge electrode is provided so as to protrude toward a liquid surface of the liquid more than the suction part, and is arranged at a position separated from the liquid surface by a certain distance.

According to the sixth particle collection vessel, since the tip portion protrudes toward the liquid surface more than the suction part, the suction part is not affected on the charged area generated by the discharge electrode so that the particles in the air flowed through the suction part can be charged surely.

The seventh particle collection vessel of a present invention includes a ground part extending toward the inside from the opening of the vessel body and coming into contact with the liquid, wherein an outer circumference of the ground part is covered by a non-conductive insulating member.

According to the seventh particle collection vessel of the present invention, since the ground part makes contact with the liquid in the vessel body by utilizing the opening of the vessel body, an additionally processing for the vessel body is unnecessary and the liquid can be easily grounded. In addition, the outer circumference of the ground part can be protected by the non-conductive insulating member to prevent the charged particles from adhering to the ground part.

In the eighth particle collection vessel of the present invention, a conductive biasing member is provided at a liquid side end portion of the ground part.

According to the eighth particle collection vessel of the present invention, even if the distance between the opening of the vessel body and the liquid surface varies due to the attachment condition of the ground part or the variation in the amount of the stored liquid, the variation in the distance between the opening of the vessel body and the liquid surface can be absorbed by the biasing member, so that the liquid can be surely grounded.

In the ninth particle collection vessel of the present invention, the suction part includes a repulsion part, and the repulsion part is provided along the liquid surface at a position separated from the liquid surface of the liquid by a certain distance.

According to the ninth particle collection vessel of the present invention, the charged particles in the air circulate so as to diffuse around the liquid surface, so that the entire liquid surface can be effectively utilized and the collection efficiency of particles can be improved. In addition, the inner space of the vessel can be effectively utilized by using the space between the repulsion part and the liquid surface as a flow path.

In the tenth particle collection vessel of the present invention, the repulsion part has a planar shape similar to the opening of the vessel body and smaller than the opening, and is supported by the other end of the suction part and by the ground part through an insulator.

According to the tenth particle collection vessel of the present invention, the repulsion part can be easily accommodated in the vessel body. In addition, the repulsion part is supported by the other end of the suction part and the ground part, so that the attachment of the repulsion part can be easily performed, and the members accommodated in the vessel body can be unitized, so that the attachment and detachment work to the vessel body can be performed easily.

In the eleventh particle collection vessel of the present invention, a main component of the liquid is water, and the liquid is formed into a liquid film having a thickness of not more than 1 mm and contains a surfactant.

According to the eleventh particle collection vessel of the present invention, a decrease in the concentration of the sample in the next processing (for example, a PCR processing or the like) can be prevented by reducing the amount of liquid. In addition, by mixing the surfactant with the liquid, viruses collected in the liquid can be inactivated and safely transferred to the next processing.

In the twelfth particle collection vessel of the present invention, the liquid contains an antioxidant.

According to the twelfth collection vessel of the present invention, it is possible to reduce the damage of genes caused by oxidative radicals generated in electric discharge and to improve the analysis accuracy after the particle sampling.

In the thirteenth particle collection vessel of the present invention, the liquid contains a deliquescent salt.

According to the thirteenth particle collection vessel of the present invention, moisture in the air can be absorbed and evaporation of the liquid can be suppressed, so that the inner surface of the vessel body can be kept wet and the particle collecting effect can be kept high.

In the fourteenth particle collection vessel of the present invention, the opening of the vessel body is formed at an upper portion facing a bottom portion of the vessel body, the bottom portion is formed flat, and an inner surface of the vessel body has a water-repellent property.

According to the fourteenth particle collection vessel, the vessel with the upper portion opened has a shape that is widely distributed in the market, so that the vessel body is easily obtainable and is excellent in an economic efficiency. In addition, because the bottom portion of the container body has a flat shape, a liquid layer with a uniform liquid surface can be formed. Therefore, the discharging performance can be stably kept. In addition, since the inner surface of the container body has a water-repellent property, the collected particles are difficult to be attached (adhered) to the inner surface of the vessel and are reliably collected by the liquid, thus improving the collecting efficiency.

In the fifteenth particle collection vessel of the present invention, the vessel body is a vial.

According to the fifteenth particle collection vessel of the present invention, since the vessel body can be sealed, the storage and transportation after the particles are collected can be carried out safely. In addition, the vial is a container used in the pharmaceutical, pharmaceutical, and sample collection fields, and has an excellent distribution (a marketability) and can be obtained at relatively low cost. In addition, since the inner surface of the vial is water-repellent, the collected particles are difficult to be attached (adhered) and reliably collected in the liquid, thus improving the collecting efficiency.

The sixteenth particle collection vessel of the present invention includes an electrode unit provided with the suction part including the discharge electrode and a power supplying contact part, the discharge part and a ground part in contact with the liquid, wherein the electrode unit is detachably provided in the opening of the vessel body.

According to the sixteenth particle collection vessel of the present invention, since the multiple members accommodated in the vessel body are unitized, if the electrode unit is attached to the opening after the liquid is supplied into the vessel body, it becomes a state of where the particles can be collected, and the usability can be improved. In addition, if the electrode unit is detached from the vessel body, the upper space of the liquid is opened, so that the liquid can be handled easily.

In the seventeenth particle collection vessel of the present invention, an upper surface of the electrode unit is formed flat, and the suction part, the discharge part and the ground part do not protrude upward from the upper surface of the electrode unit.

According to the seventeenth particle collection vessel of the present invention, the lid can be attached surely so that a sealing property (a tight-closing property) can be ensured.

The first particle collection device is a particle collection device provided with the particle collection vessel, the particle collection device includes: a power supplying unit detachably attached to the particle collection vessel, wherein the power supplying unit includes: a suction flow path which can be communicated with the inflow path of the suction part; a discharge flow path which can be communicated with the outflow path of the discharge part; a power supplying member which can come into contact with a power supplying contact member formed in the suction part; and a ground member which can come into contact with a ground part in contact with the medium.

According to the first particle collection device of the present invention, the suction flow path, the discharge flow path, the power supplying member and the ground member are integrated into the power supplying unit, so that the charging and collecting work of the particles in the air can be easily performed by setting the particle collection vessel in the particle collection device and attaching the power supplying unit to the vessel body.

The second particle collection device of the present invention includes: an opening/closing valve provided in an upstream flow path of the suction flow path of the power supplying unit; and a suction means provided in a downstream flow path of the discharge flow path of the power supplying unit, wherein in operation, the suction means is controlled to be operated continuously and the opening/closing valve is controlled to be alternately opened and closed.

According to the second particle collection device of the present invention, when the closing action of the opening/closing valve is performed while the suction means is continuously sucking, the pressure in the container is increased, and when the opening/closing valve is subsequently switched to the opening action, the speed toward the liquid surface of the air containing the particles sucked from the suction port is increased, and the air impinges on the liquid surface vigorously, so that the degree to which the particles are brought into contact with and mixed with the medium is improved, and the collection efficiency of the particles in the air can be enhanced.

The third particle collection device of the invention, in the operation, the opening/closing valve is controlled so that an opened time is longer than a closed time.

According to the third particle collection device of the present invention, the collection efficiency can be improved while the effect of the collection degree of particles per hour is kept low by controlling the opened time to be longer than the closed time.

The first particle collection method in which particles in air are collected using the particle collection device, the particle collection method includes: a medium supplying process in which the medium is supplied into the vessel body; an air sucking process in which air containing particles is sucked into the vessel body after the medium supplying process; a particle charging process in which particles in the air sucked in the air sucking process are charged by applying a high voltage to the discharge electrode; and a particle collecting process in which the particles charged in the particle charging process are collected in the medium supplied into the vessel body at the medium supplying process.

According to the first particle collection method of the present invention, the particles in the air are always charged, sucked into the vessel, mixed with the medium stored at the bottom portion and then collected, so that the medium can be effectively utilized. In addition, since the particles in the air are collected in the medium in the vessel, each processing (For example, a PCR processing, and the like) in the next process after the particles are collected can be easily performed.

In the second particle collection method of the present invention, the particles contain microorganisms, bacteria and viruses.

According to the second particle collection method of the present invention, microorganisms, bacteria and viruses can be efficiently collected.

Effect of Invention

According to the present invention, various excellent effects can be obtained such as excellent economic efficiency, easy performing a processing in the next process after the particles are collected, and improvement in the charging performance and the collecting performance.

EMBODIMENT FOR CARRYING OUT THE INVENTION

Hereinafter, with reference to the attached drawings, an embodiment of the present invention will be described. In the following descriptions, "upstream", "downstream" and similar terms refer to "upstream", "downstream" and similar concepts in the direction of air flow.

Figure 1:
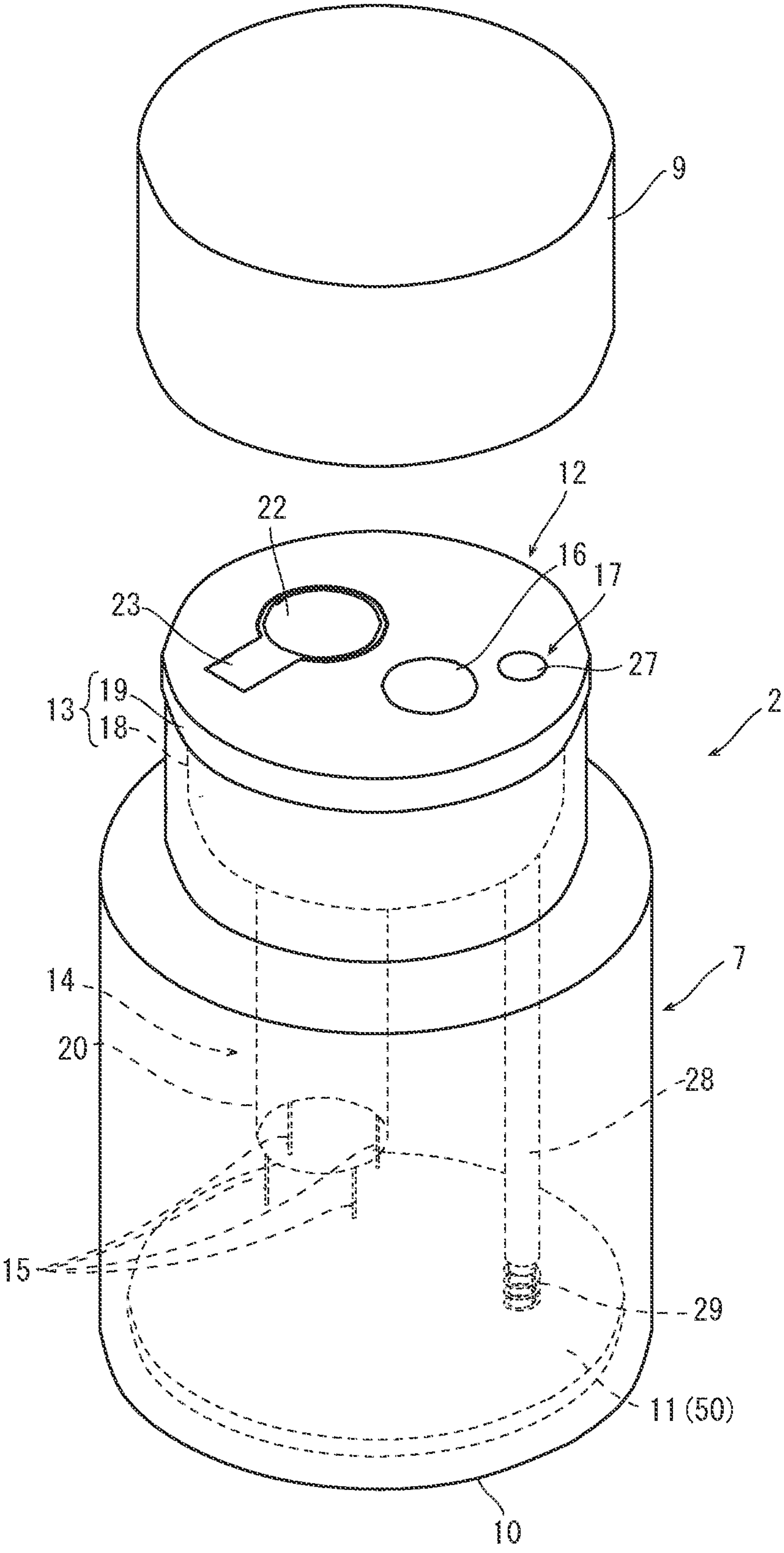
FIG. 1 is a disassembled perspective view showing a particle collection vessel according to one embodiment of the present invention, viewed from an oblique upper side.
Figure 2:
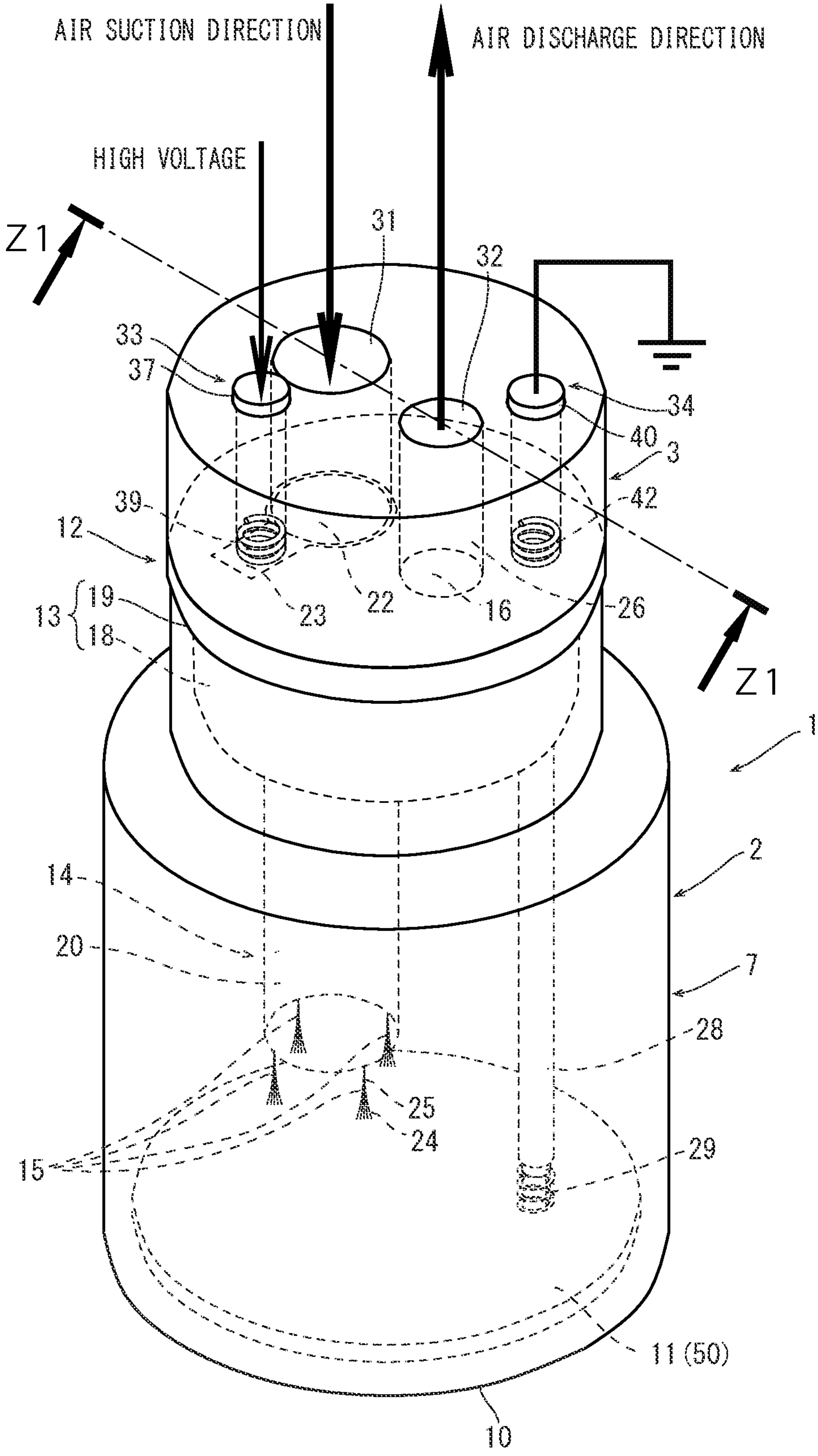
FIG. 2 is a perspective view showing a particle collection device according to the embodiment of the present invention, viewed from an oblique upper side.
Figure 3:
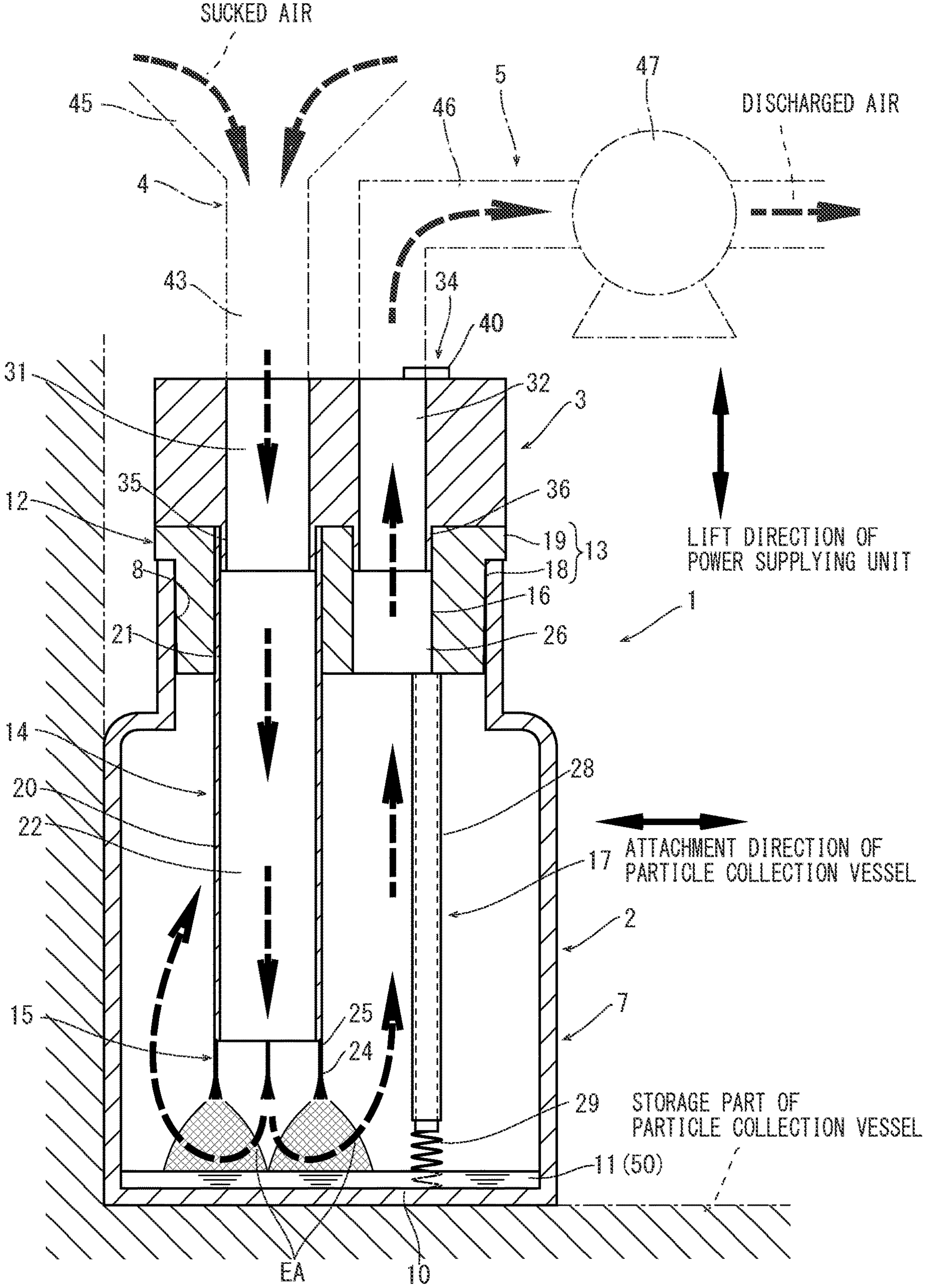
FIG. 3 is a sectional view taken along the line Z1-Z1 in FIG. 2.
Figure 4A:
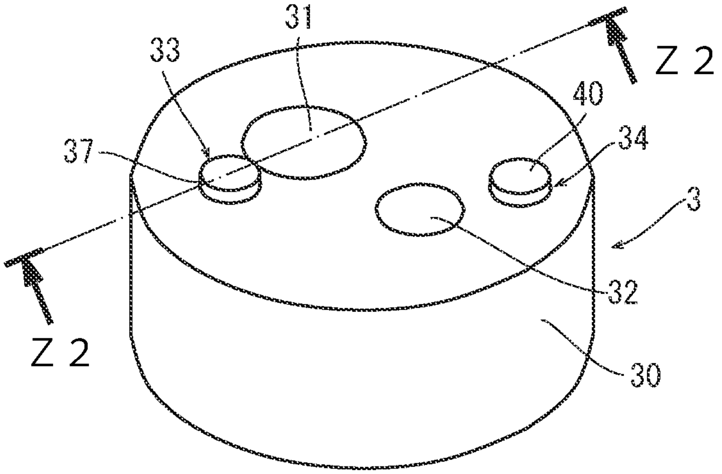
FIG. 4A is a perspective view showing a power supplying unit of the particle collection device according to the embodiment of the present invention, viewed from an oblique upper side.
Figure 4B:
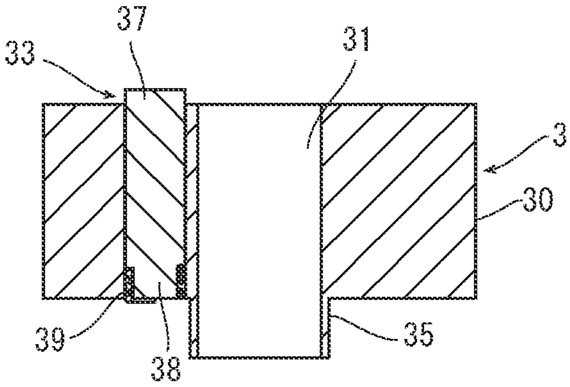
FIG. 4B is a sectional view taken along the line Z2-Z2 in FIG. 4A.
Figure 4C:
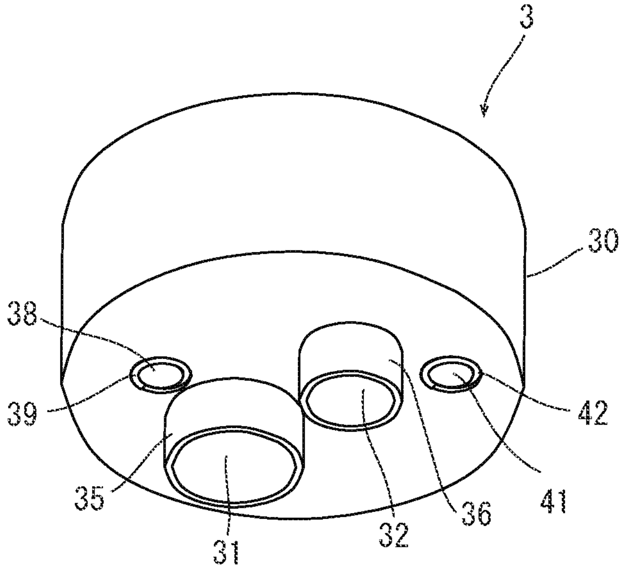
FIG. 4C is a perspective view showing the power supplying unit of the particle collection device according to the embodiment of the present invention, viewed from an oblique lower side.

[Particle Collection Device] First, with reference to FIG. 1 to FIG. 4C, the particle collection device according to the embodiment of the present invention will be described. FIG. 1 is a disassembled perspective view showing a particle collection vessel according to the embodiment of the present invention, viewed from an oblique upper side, FIG. 2 is a perspective view showing the particle collection device according to the embodiment of the present invention, viewed from an oblique upper side, FIG. 3 is a sectional view taken along the line Z1-Z1 in FIG. 2, FIG. 4A is a perspective view showing a power supplying unit of the particle collection device according to the embodiment of the present invention, viewed from an oblique upper side, FIG. 4B is a sectional view taken along the line Z2-Z2 in FIG. 4A, and FIG. 4C is a perspective view showing the power supplying unit of the particle collection device according to the embodiment of the present invention, viewed from an oblique lower side.

The particle collection device 1 according to the embodiment is a device which charges airborne particles and then collects them, and the airborne particles to be collected by the particle collection device 1 include not only dust but also bio-particles such as microorganisms, bacteria and viruses. The particle collection device 1 is provided with a particle collection vessel 2 which is attachably and detachably provided in the particle collection device 1, a power supplying unit 3 which is detachably attached to the particle collection vessel 2, a suction equipment 4 which causes air to flow into the particle collection vessel 2, a discharge equipment 5 which causes the air to flow out of the particle collection vessel 2, and a controller 6 (see FIG. 10) which controls the particle collection device 1.

<Particle collection Vessel> The particle collection vessel 2 includes a vessel body 7 having a bottomed cylindrical shape with the upper portion narrowed. The upper end portion of the vessel body 7 has an opening 8, and the vessel body 7 is configured such that the opening 8 can be sealed (tightly closed) by a lid 9. By making the vessel body 7 sealable (tightly closable), it is possible to safely store and transport the vessel after the bio-particles are collected.

The vessel body 7 is preferably a vial made by glass, but may be made of plastic. A water repellent coating treatment (for example, a silicon coating, a Teflon (R) coating and the like) may be applied to the inner surface of the vessel body 7. In a case where the vessel body 7 is a vial, a rubber stopper is inserted into the opening 8 so that it has a highly airtight property and has a low risk of contamination. In addition, since it is made of glass, the substance stored in the vessel body 7 is hardly affected by chemical alteration derived from the vessel body 7, so that the substance can be stored stably for a long time. Furthermore, a vial is used in a wide range of research facilities and analytical institutions, and has a highly marketability. Furthermore, since the glass which is a raw material of the vial has a water-repellent property, it is possible to suppress the adhering of collected viruses to the inner surface of the vessel body 7 as small as possible without applying the water-repellent coating treatment to the inner surface of the vessel body 7.

Preferably, the bottom portion 10 of the vessel body 7 has a flat shape, and the vessel body 7 has a medium storage part 50 in which the medium can be stored in a film shape on the bottom portion 10. The bottom portion 10 of the vessel body 7 does not necessarily have a flat shape, but may be a non-flat shape with a raised center, in which case a film may be formed thicker.

The medium is a conductive liquid 11, but may be a gel, a jelly or a powder. The main component of the liquid 11 is water (for example, pure water, sterile water, distilled water), and a substance mixed with the liquid 11 is surfactant (for example, AVL buffer), antioxidant (for example, glucose), salt, antioxidant (for example, vitamin C), glucose and antievaporation agent (for example, glycerin).

The concentration of the surfactant is set at several %, specifically about 5%. The surfactant may also reduce surface tension and improve wettability so that the liquid spreads more easily to the glass surface. By mixing the surfactant with water, the virus can be detoxified.

In addition, by mixing the antioxidant with water, it is possible to reduce the damage of genes by oxidative radicals generated in electrical discharge, and to improve analysis accuracy after the particle sampling.

The concentration of salt is set at several %, specifically about 2%. By mixing deliquescent salt with water, moisture in the air can be absorbed and evaporation of the liquid can be suppressed, so that the inner surface of the vessel body 7 can be kept wet and the particle collection effect can be kept high.

In addition, by mixing antioxidants (vitamin C) and glucose with water, it is possible to relieve DNA stress. And, by mixing anti-evaporation material with water, it is possible to prevent evaporation of the liquid.

The liquid 11 is supplied to the medium storage part 50 so as to form a liquid film having a thickness of not more than 2 mm, preferably not more than 1 mm. The liquid film is sufficient to collect the bio-particles from the air, and by reducing the amount of liquid to be collected, it is possible to prevent the sample concentration from decreasing in the next processing (for example, a PCR processing). In addition, by forming the liquid film, even if the particle collection vessel 2 is slightly tilted, there is no possibility that the liquid 11 leaks to the outside. Moreover, it is not necessary to mix enzyme (reagent) for identifying microorganisms in advance in the liquid film. This is because it is preferable to mix enzyme before the post-collection processing (for example, a PCR processing) because the enzyme is not weakened.

An electrode unit 12 is detachably provided in the opening 8 of the vessel body 7. The electrode unit 12 includes a supporting body 13, a suction part 14, a discharge electrode 15, a discharge part 16 and a ground part 17.

The supporting body 13 is made of non-conductive material, and may be formed, for example, by processing a rubber plug. The supporting body 13 has a columnar trunk part 18 detachably attached to the opening 8 of the vessel body 7 and a flat columnar flange part 19 formed above the trunk part 18. With the flange part 19 serving as a stopper, the supporting body 13 can be prevented from falling inside the vessel body 7. The upper surface of the supporting body 13 has a flat shape. Therefore, the lid 9 can be closed securely to seal the inside of the vessel body 7 after the particle sampling, thereby preventing the particles from scattering outside the vessel body 7.

The suction part 14 has a circular cylindrical body 20 elongated in the longitudinal direction. The cylindrical body 20 may have a cylindrical shape other than a circular cylindrical shape, such as a polygonal cylindrical shape. The cylindrical body 20 penetrates the supporting body 13 in the upper-and-lower direction, and the upper portion 21 is supported by the supporting body 13. The upper end of the cylindrical body 20 is opened to the outside of the vessel body 7, and an inflow path 22 is formed inside the cylindrical body 20. A plate-like power supplying contact part 23 is projected from one circumferential edge of the upper end of the cylindrical body 20 along the upper surface of the supporting body 13 (see FIG. 1). The cylindrical body 20 is supported by the supporting body 13 with its upper end and the power supplying contact part 23 flat with the upper surface of the supporting body 13.

In the vessel body 7, the cylindrical body 20 extends downward toward the liquid 11. The discharge electrode 15 is protruded downward from the lower end of the cylindrical body 20. The cylindrical body 20 is made of conductive stainless steel (SUS304), and is made of the same material as the discharge electrode 15. By using the same material for the cylindrical body 20 and the discharge electrode 15, electrolytic corrosion (electrocorrosion) caused by contact between different metals can be prevented.

The Discharge electrodes 15 are intermittently provided at predetermined intervals along the circumferential direction of the cylindrical body 20. Thus, the microorganisms in the air sucked into the vessel body 7 can be uniformly and evenly charged. In the illustrated example, four bundles of the discharge electrodes 15 are arranged at 90 degrees intervals, but other arrangements may be used, for example, six bundles may be arranged at 60 degrees intervals.

The discharge electrodes 15 are all formed to have approximately the same total length, and the tips of the discharge electrodes 15 are approximately aligned. Each discharge electrode 15 has a bundle 25 formed in a brush shape by bundling fibrous wire electrodes 24. The wire electrode 24 is made of a non-magnetic stainless steel fiber having a diameter of 12 μm. Therefore, the wire electrode 24 is separated from the bundle 25 easily, and the discharging performance can be enhanced. On the other hand, for example, in a ferrite series having a magnetic property, since the wire electrode 24 is more difficult to separate from the bundle 25, the effect of electric field interference with the bundle 25 is large, and it is difficult to generate a corona discharge having a strong electric field.

One discharge electrode 15 is formed, for example, by bundling about one hundred wire electrodes 24. The discharge electrode 15 may be formed by bundling ten to two hundreds wire electrodes 24 having a diameter of 5 to 25 μm. Alternatively, the discharge electrode 15 may be formed of a carbon fiber having a diameter of 5 to 7 μm. In this example, the discharge electrode 15 is formed by the wire electrode 24, but it may be formed by a needle electrode or a plate-like electrode with protrusions.

The voltage applied to the discharge electrode 15 is several kV, specifically in the range of 4 to 6 kV. The length of the discharge electrode 15 (the length protruding from the cylindrical body 20) is several mm, specifically in the range of 3 to 7 mm. This allows stable discharging even at relatively low voltages.

A positive high voltage is applied to the discharge electrode 15 by direct current. By adopting the DC method in this way, a relatively simple configuration can be made compared to other methods (AC, pulse). In particular, when collecting bio-particles such as microorganisms, bacteria and viruses, the voltage applied to the electrode is set to a voltage (for example, several kV) that does not destroy the cells of the bio-particles. In addition, by adopting the positive charging method as an application method of high voltage, it is possible to suppress the production of ozone compared to the negative charging method, so that the effect on bio-particles such as microorganisms, bacteria and viruses in particular can be reduced.

In the illustrated example, a high voltage at which a corona discharge is generated is applied to the discharge electrode 15, but an inductive charging, in which particles (all particles) are charged by applying a high voltage at which a corona discharge is not generated (a voltage lower than the corona discharge voltage), may be adopted.

The discharge part 16 has an outflow path 26 formed by hollowing out the inside of the supporting body 13. The outflow path 26 has a circular columnar shape, and is formed to penetrate the inside of the supporting body 13 in the upper-and-lower direction. The outflow path 26 is formed parallel to the cylindrical body 20 of the suction part 14, and is arranged so as to be away from the cylindrical body 20 as far as possible in a plan view. The outflow path 26 may be formed inside the supporting body 13 by housing the cylindrical body inside the supporting body 13.

The ground part 17 is conductive, and formed in a circular rod shape elongated in the longitudinal direction. The shape of the ground part 17 may be have a plate-like shape or a cylindrical shape. The ground part 17 penetrates the supporting body 13 in the upper-and-lower direction, and the upper portion is supported by the supporting body 13. At the upper end portion of the ground part 17, a ground contact part 27 having a one size larger outer diameter is formed (see FIG. 1). The ground part 17 is supported by the supporting body 13 with the upper surface of the ground contact part 27 flat with the upper surface of the supporting body 13.

In the vessel body 7, the ground part 17 extends downward toward the liquid 11, and is covered by a non-conductive, cylindrical, for example, resin insulating member 28. Since the ground part 17 is thus covered with the insulating member 28 in the vessel body 7 and protected, the charged particles can be prevented from adhering to the ground part 17.

A ground spring 29 is connected to the lower end portion of the ground part 17 as a conductive biasing member, and the ground spring 29 comes into elastic contact with the bottom portion 10 of the vessel body 7. Therefore, even if the distance between the opening 8 of the vessel body 7 and the liquid surface varies depending on the attachment condition of the supporting body 13 or the variation in the storage amount of the liquid 11, the variation in the distance is absorbed by the ground spring 29, so that the ground spring 29 comes into contact with the liquid 11 and the liquid 11 can be surely grounded. In the illustrated example, a coil spring is used as the biasing member, but a leaf spring may be used.

By constructing the electrode unit 12 in this way, as shown in FIG. 1, the upper surface of the electrode unit 12 is formed flat, and the suction part 14, the discharge part 16 and the ground part 17 do not project upward from the upper surface of the electrode unit 12. Therefore, since the lid 9 can be securely attached to the particle collection vessel 2, a sealing property (a tightly closing property) of the vessel body 7 can be ensured.

In addition, by attaching the electrode unit 12 to the opening 8 of the vessel body 7, the process of accommodating the discharge electrode 15 in the vessel body 7 and the process of accommodating the ground part 17 in the vessel body 7 and making contact with the liquid 11 are carried out simultaneously, so that the efficiency of the work can be improved.

<Power Supplying Unit>

As shown in FIG. 2 to FIG. 4C, the power supplying unit 3 is provided above the electrode unit 12 so as to be lifted and lowered manually (or automatically) (see the thick arrow in the upper-and-lower direction in FIG. 3), and when the particle collection vessel 2 is set in a predetermined position in the particle collection device 1 and then the power supplying unit 3 is lowered toward the particle collection vessel 2, the power supplying unit 3 and the electrode unit 12 are closely connected. The power supplying unit 3 includes a supporting body 30, a suction flow path 31, a discharge flow path 32, a power supplying member 33 and a ground member 34.

The supporting body 30 is formed of a non-conductive member, and made of resin (or rubber), for example. The supporting body 30 has a circular columnar shape with the same diameter as the flange part 19 of the supporting body 13 of the electrode unit 12.

The suction flow path 31 has a circular columnar shape, and is formed to penetrate the supporting body 30 in the upper-and-lower direction. The suction flow path 31 is arranged at a position corresponding to the inflow path 22 of the suction part 14 of the electrode unit 12, and can be communicated with the inflow path 22 of the suction part 14. At the lower end of the suction flow path 31, an extending part 35 extending downward (toward the electrode unit 12) is formed, and the extending part 35 can fit into the upper end portion of the cylindrical body 20 of the suction part 14.

The discharge flow path 32 has a circular columnar shape, and is formed to penetrate the supporting body 30 in the upper-and-lower direction parallel to the suction flow path 31. The discharge flow path 32 is arranged at a position corresponding to the outflow path 26 of the discharge part 16 of the electrode unit 12, and can be communicated with the outflow path 26 of the discharge part 16. At the lower end of the discharge flow path 32, an extending part 36 extending downward (toward the electrode unit 12) is formed in the same way as the suction flow path 31, and the extending part 36 can fit into the upper end portion of the outflow path 26 of the discharge part 16.

Since the extending parts 35 and 36 are formed in the suction flow path 31 and the discharge flow path 32 respectively, when the power supplying unit 3 is connected to the electrode unit 12, the extending part 35 of the suction flow path 31 of the power supplying unit 3 is fitted into the suction part 14 of the electrode unit 12 and the extending part 36 of the discharge flow path 32 of the power supplying unit 3 is fitted into the discharge part 16 of the electrode unit 12, so that air leakage can be prevented.

The power supplying member 33 is formed in a circular columnar shape, made of conductive material, penetrates the inside of the supporting body 30 in the upper-and-lower direction, and is fixed at a position corresponding to the power supplying contact part 23 of the suction part 14 of the electrode unit 12. The upper end portion 37 of the power supplying member 33 projects slightly upward from the upper surface of the supporting body 30, and a high voltage is applied through the upper end portion 37. The lower end portion 38 of the power supplying member 33 has an outer diameter one size smaller, and a power supplying spring 39 is wound around and fixed to the outer circumference of the lower end portion 38. Thus, when the power supplying unit 3 and the electrode unit 12 come into close contact with each other, the power supplying spring 39 and the power supplying contact part 23 come into contact with each other.

The ground member 34, like the power supplying member 33, is formed in a circular cylindrical shape, made of conductive material, penetrates the inside of the supporting body 30 in the upper-and-lower direction, and is fixed at a position corresponding to the ground contact part 27 of the ground part 17 of the electrode unit 12. The upper end portion 40 of the ground member 34 projects slightly above the upper surface of the supporting body 30, and is grounded through the upper end portion 40. The lower end portion 41 of the ground member 34 has an outer diameter one size smaller, and a ground spring 42 is wound around and fixed to the outer circumference of the lower end portion 41. Thus, when the power supplying unit 3 and the electrode unit 12 come into close contact with each other, the ground spring 42 and the ground contact part 27 come into contact with each other.

<Suction Equipment> As shown in FIG. 3, the suction equipment 4 includes an upstream flow path 43 connected to the suction flow path 31 of the power supplying unit 3 and a suction port 45 provided at the upstream end of the upstream flow path 43. The suction port 45 is widened in a funnel-like shape so as to facilitate suction of air containing particles. Although not particularly illustrated, the suction equipment 4 may include a pre-treatment filter for collecting relatively large particles such as dust and a mist sprayer. When a mist sprayer (the solution to be sprayed is, for example, pure water) is provided, since the mist is sucked with the air into the vessel body 7, even if the liquid evaporates, it can be replenished.

<Discharge Equipment> As shown in FIG. 3, the discharge equipment 5 includes a downstream flow path 46 connected to the discharge flow path 32 of the power supplying unit 3, a pump 47 as a suction means provided in the middle of the downstream flow path 46 and a discharge port (not shown) provided at the downstream end of the downstream flow path 46. Although a fan may be used as the suction means, the pump 47 is preferable because its suction pressure is higher. Although not particularly illustrated, the discharge equipment 5 may include a HEPA filter for collecting relatively small particles.

Figure 5:
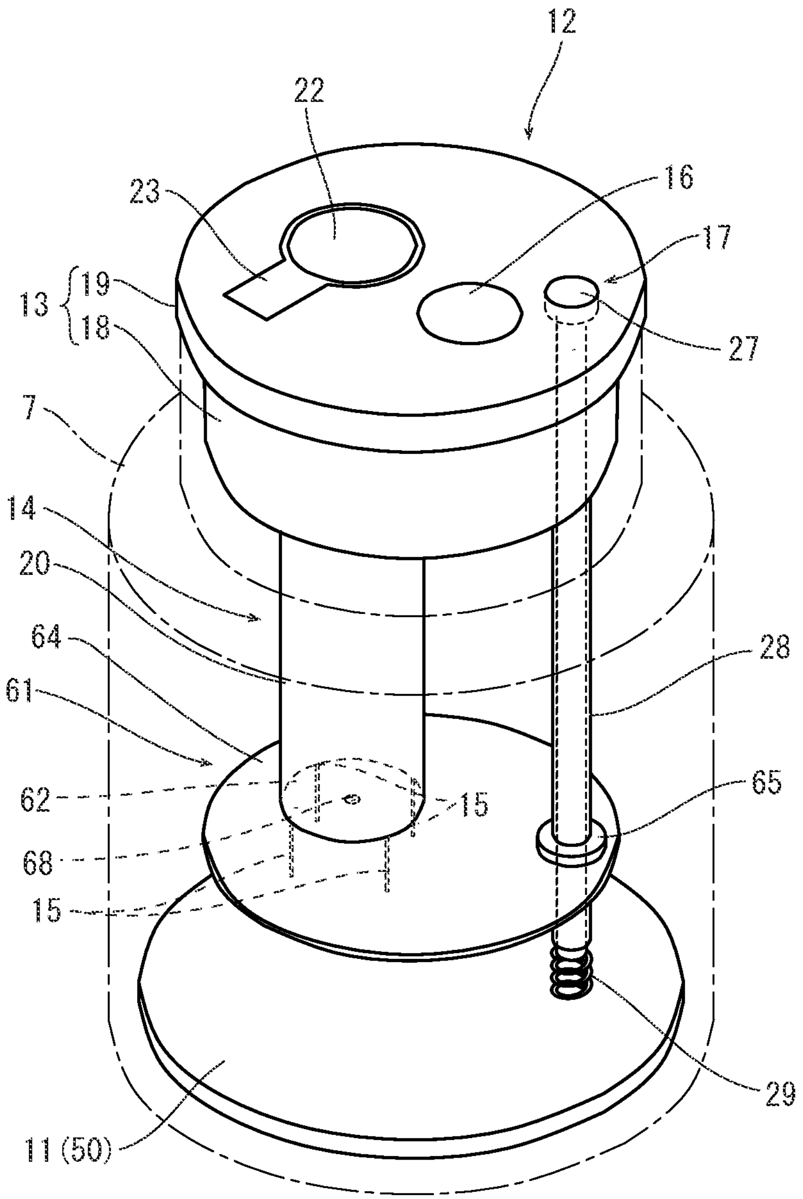
FIG. 5 a perspective view showing another type of the particle collection vessel according to the embodiment of the present invention, viewed from an oblique upper side.
Figure 6:
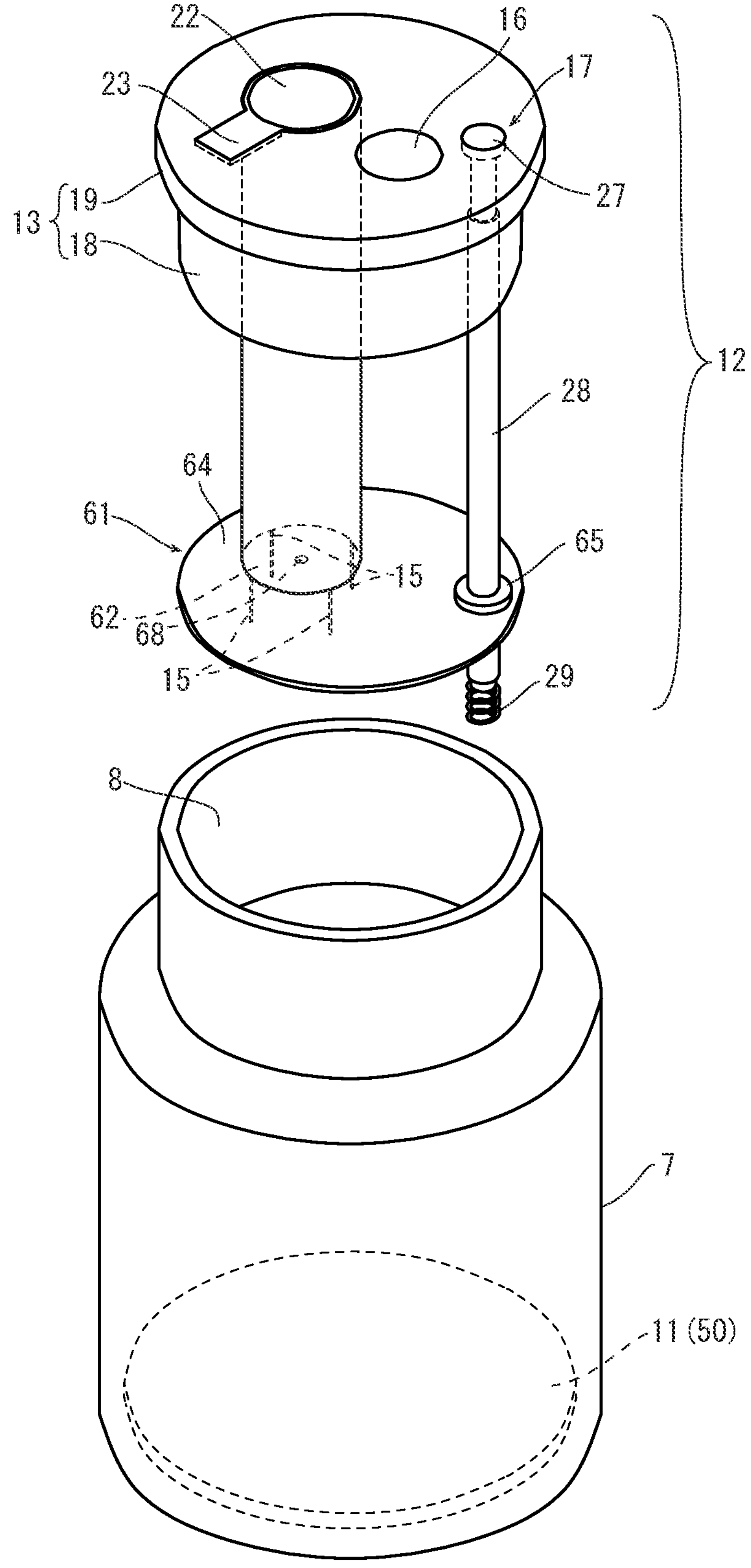
FIG. 6 is a disassembled perspective view showing a state where an electrode unit is detached from another type of the particle collection vessel according to the embodiment of the present invention, viewed from an oblique upper side.
Figure 7:
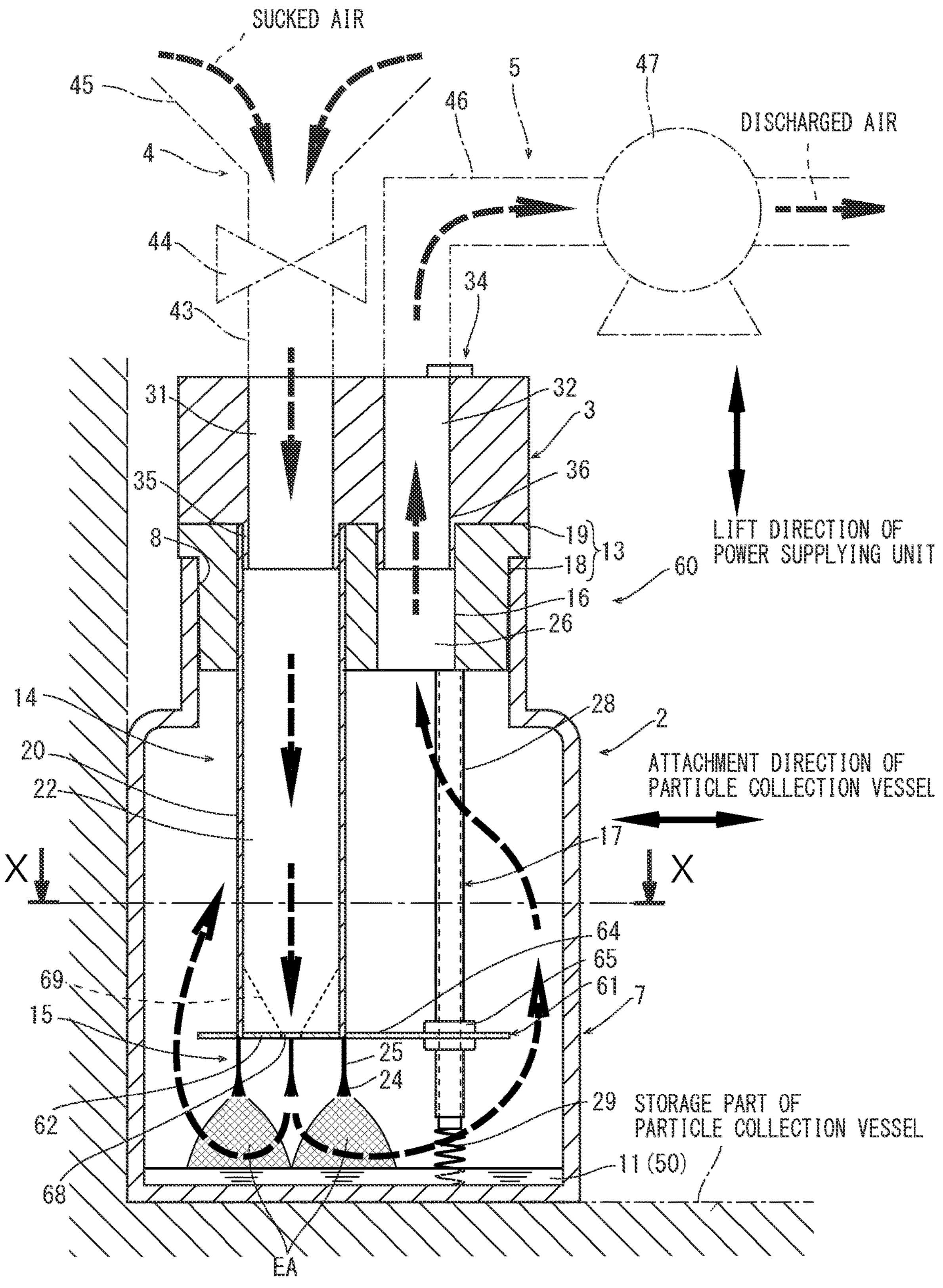
FIG. 7 is a sectional view showing another type of the particle collection device according to the embodiment of the present invention.
Figure 8:
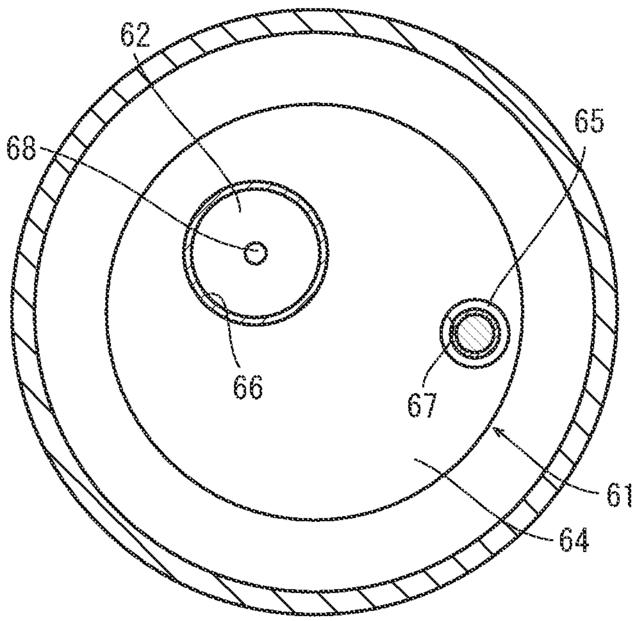
FIG. 8 is a sectional view taken along the line X-X in FIG. 7.

[Another Type of Particle Collection Device] Next, with reference to FIG. 5 to FIG. 8, another type of particle collection device according to the embodiment of the present invention will be described. FIG. 5 a perspective view showing another type of the particle collection vessel according to the embodiment of the present invention, viewed from an oblique upper side, FIG. 6 is a disassembled perspective view showing a state where an electrode unit is detached from another type of particle collection vessel according to the embodiment of the present invention, viewed from an oblique upper side, FIG. 7 is a sectional view showing another type of particle collection device according to the embodiment of the present invention, and FIG. 8 is a sectional view taken along the line X-X in FIG. 7. In the description of another type of the particle collection device according to the embodiment of the present invention, for convenience of explanation, the same configurations as those of the above particle collection device 1 are marked with the same references as those of FIG. 1 to FIG. 4C, and their detailed descriptions are omitted.

In another type of the particle collection device 60 according to the present embodiment, the particle collection vessel 2 includes a repulsion part 61 and a jetting plate 62, in addition to the same configurations as the particle collection device 1 described above. In the suction equipment 4, a solenoid valve 44 as an opening/closing valve is provided in the middle of the upstream flow path 43.

<Repulsion Part> The repulsion part 61 includes a circular flat repulsion plate 64, and the outer diameter of the repulsion plate 64 is set to be one size smaller than the opening 8 of the vessel body 7. The repulsion plate 64 is fixed to the lower end of the cylindrical body 20 of the suction part 14, and is supported by the insulating member 28 of the ground part 17 through a bush 65 which is a non-conductive insulator. In the repulsion plate 64, circular openings 66 and 67 are formed at positions corresponding to the cylindrical body 20 and the bush 65, respectively (see FIG. 8).

The repulsion plate 64 is arranged so as to face the liquid surface of the liquid in the vessel body 7. The distance between the repulsion plate 64 and the liquid surface is set to be larger than the distance between the tip end portion (the lower end portion) of the discharge electrode 15 and the liquid surface. A clearance as an air flow path is provided between the inner surface of the vessel body 7 and the outer circumference of the repulsion plate 64.

The applied voltage (the high voltage) applied to the repulsion plate 64 is set to the same several KV as that of the discharge electrode 15. The electrode unit 12 including the repulsion plate 64 can be accommodated in the vessel body 7 and detached from the vessel body 7 through the opening 8 of the vessel body 7. This facilitates handling it as the electrode unit 12. In addition, if the electrode unit 12 is detached from the vessel body 7, the upper space of the liquid layer (the liquid film) becomes an open state, so that the liquid 11 can be handled easily. Furthermore, it is possible to easily form a liquid layer on the plate by using a dropper or the like and to collect the liquid 11 after the particles are collected.

<Jetting Plate> The jetting plate 62 is provided in the opening 66 formed at a position corresponding to the cylindrical body 20 of the repulsion plate 64. The jetting plate 62 is arranged at a position facing the liquid surface with a predetermined distance from the liquid surface. At the center portion of the jetting plate 62, a small-diameter jetting port 68 is formed to allow air to flow out vigorously. The diameter of the jetting port 68 is set to be not more than 1 mm, and for example, when the inner diameter of the cylindrical body 20 is about 10 mm, it is set to be about 0.5 mm.

In the illustrated example, the jetting plate 62 is provided, but instead of the jetting plate 62, for example, an inclined part 69 may be provided such that the opening area of the suction part 14 gradually decreases from the upstream side to the downstream side of the cylindrical body 20 (see the broken line in FIG. 7).

In addition, in the illustrated example, since the repulsion plate 64 and the jetting plate 62 are arranged at the same height at the lower end portion of the cylindrical body 20 of the suction part 14, the repulsion plate 64 and the jetting plate 62 may be formed into one circular plate as one unit. Furthermore, various modifications other than the above examples are possible, for example, only one of the jetting plate 62 and the repulsion plate 64 may be provided.

Figure 9:
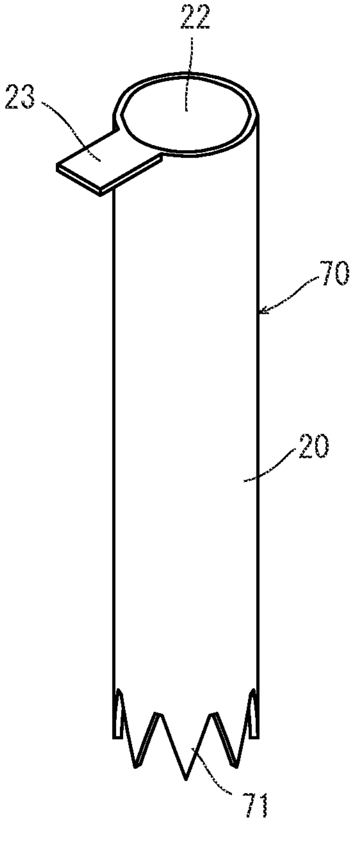
FIG. 9 is a perspective view showing a modified example of a suction part of the particle collection vessel according to the embodiment of the present invention.

<Modified Examples of Suction Part> FIG. 9 shows a suction part 70 of a modified example of the above particle collection device 1 and another type of the particle collection device 60. The suction part 70 of the modified example has a saw-toothed discharge electrode 71 around the lower end portion of the cylindrical body 20 instead of the brush-shaped discharge electrode 15 described above. By forming pointed tip portions on the discharge electrode 71, an unequal electric field can be generated at the tip portions and the electric field can be concentrated, so that the particles can be charged.

Figure 10:
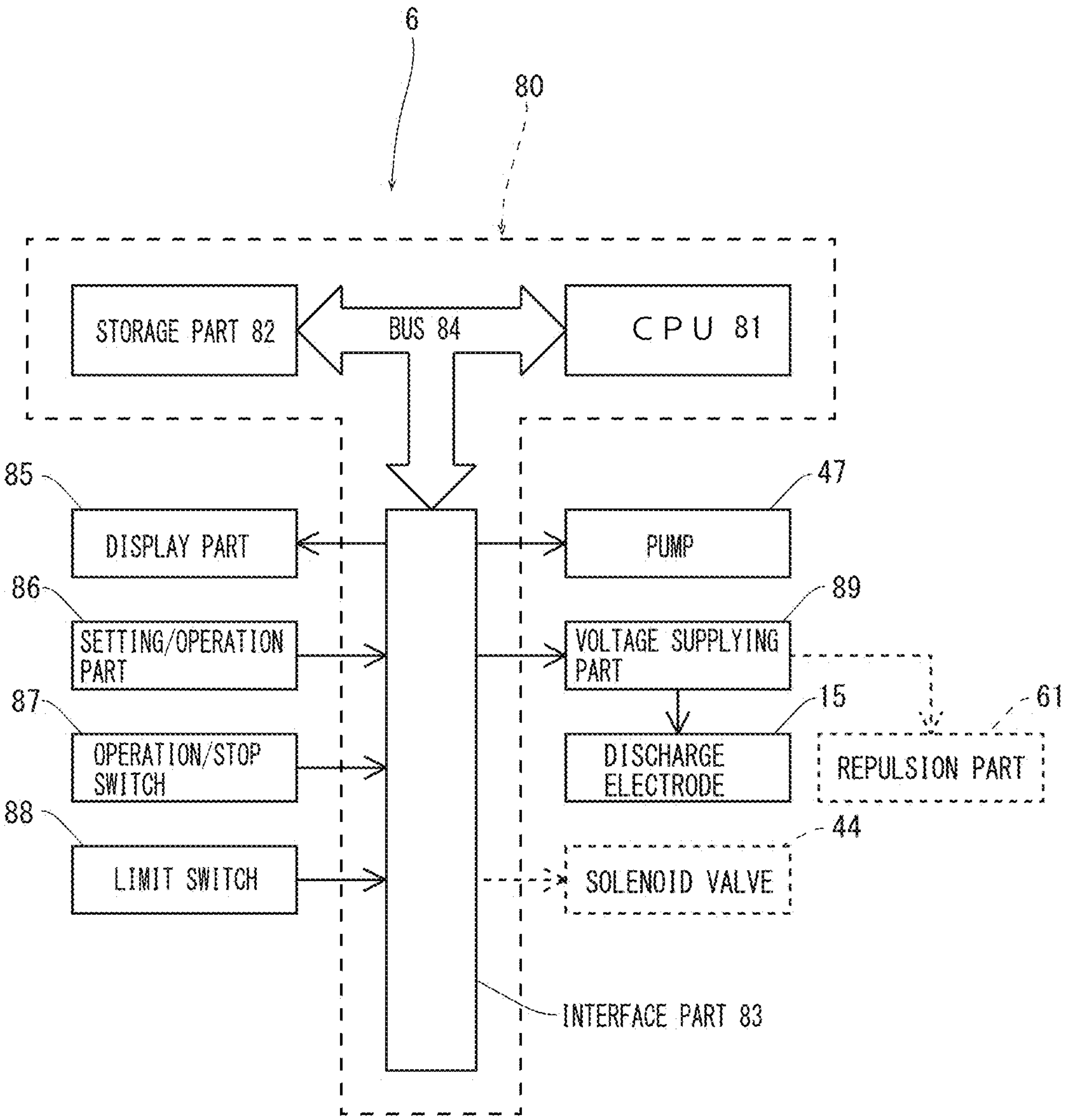
FIG. 10 is a block diagram showing a configuration of the particle collection device according to the embodiment of the present invention.

<Controller> As shown in FIG. 10, the controller 6 includes a control unit 80, and the control unit 80 is composed of a CPU 81, a storage part 82 and an interface part 83 which are connected to each other by a bus 84. To the control unit 80, a display part 85, a setting operation part 86, an operation/stop switch 87, a limit switch 88, the pump 47, a voltage supplying part 89, the solenoid valve 44 and the others are connected via the interface part 83. A battery is installed as the power supply, although not illustrated. Although not illustrated in particular, a cooling means (for example, the Peltier element) for cooling the vessel body 7 (especially the bottom portion 10 where the liquid 11 is stored) may be provided. By the cooling means, the liquid 11 stored in the vessel body 7 can be cooled and evaporation of the liquid can be prevented.

When the operation/stop switch 87 is turned ON, the pump 47 starts sucking air, and a predetermined high voltage is applied to the discharge electrodes 15, 71 and the repulsion part 61 by the voltage supplying part 89. At this time, the limit switch 88 (a safety switch) detects whether the particle collection vessel 2 is accommodated in a predetermined position, and the pump 47 does not start the sucking operation unless the limit switch 88 is turned on. The pump 47 may be controlled to stop the sucking operation for a preset operating time after sucking the air.

[Particle Collection Method] With reference to FIG. 1 to FIG. 11, a particle collection method using the particle collection devices 1 and 60 to collect airborne particles will be described.

The particle collection method according to the embodiment of the present invention includes: a liquid supplying process in which the lid 9 of the particle collection vessel 2 is detached and the conductive liquid 11 is suppled in the vessel body 7 through the opening 8; a collection vessel installing process in which the particle collection vessel 2 with the electrode unit 12 attached to the opening 8 is set in the storage part of the particle collection vessel 2 after the liquid supplying process and the power supplying unit 3 is connected to the electrode unit 12 manually or automatically; an air sucking process in which the particle collection devices 1 and 60 are started to be driven after the collection vessel installation process and suck the air containing particles into the vessel body 7; a particle charging process in which a high voltage is applied to the discharge electrode 15 (and the repulsion part 61) to charge the particles in the air sucked in the air sucking process; and a particles collecting process in which the liquid 11 supplied into the vessel body 7 is caused to collect the particles charged in the particle charging process. The air sucking process, the particle charging process and the particle collecting process are performed according to the continuous or intermittent operations described below.

<Continuous Operation> First, with reference to FIG. 2, FIG. 3 and FIG. 10, the action in the continuous operation performed in the particle collection device 1 will be described.

In the case of continuous operation, when the operation/stop switch 87 is turned on, based on a command from the CPU 81, a high voltage V1 is applied from the voltage supplying part 89 to the discharge electrode 15 of the electrode unit 12 through the power supplying member 33 of the power supplying unit 3, and the pump 47 is driven.

By driving the pump 47, dust-containing air containing particles such as bio-particles and dust is sucked from the suction port 45 into the vessel body 7 through the suction flow path 31 and the cylindrical body 20 of the suction part 14, is lowered, then diffuses to the surroundings along the liquid surface and then passes between the discharge electrode 15 and the liquid surface. At this time, a charged area EA is formed between the lower end portions (the tip portions) of the discharge electrode 15 and the liquid surface by a corona discharge generated between the lower end portions (the tip portions) of the discharge electrode 15 and the liquid surface.

Then, the particles in the air passing between the discharge electrode 15 and the liquid surface are charged and attracted to the liquid surface by passing through the charged area EA formed between the lower end portions (the tip portions) of the discharge electrode 15 and the liquid surface by a corona discharge, and then are collected by the liquid 11.

The clean air generated such that the particles are removed from the air and collected in the liquid 11 is discharged to the outside from the discharge port through the flow path 46 of the discharge equipment 5 from the outflow path 26 of the discharge part 16 of the electrode unit 12 and the discharge flow path 32 of the power supplying unit 3.

Then, when the operation/stop switch 87 is turned off, based on a command from the CPU 81, the application of high voltage to the discharge electrode 15 is stopped, and the pump 47 is stopped.

<Intermittent Operation> Next, with reference to FIG. 7, FIG. 10 and FIG. 11, the action in the intermittent operation performed in the particle collection device when a high collection efficiency is required will be described.

In the case of intermittent operation, when the operation/stop switch 87 is turned on, based on a command from the CPU 81, the solenoid valve 44 is switched from the closed state to the opened state, a high voltage V1 is applied from the voltage supplying part 89 to the discharge electrode 15 and the repulsion plate 64 through the power supplying member 33 of the power supplying unit 3, and the pump 47 is driven.

By driving the pump 47, the particles in the dust-containing air sucked into the vessel body 7 are charged and attracted to the liquid surface by passing through the charged area EA, repelled against the repulsion plate 64, attracted to the liquid surface side, and are collected by the liquid 11.

Figure 11:
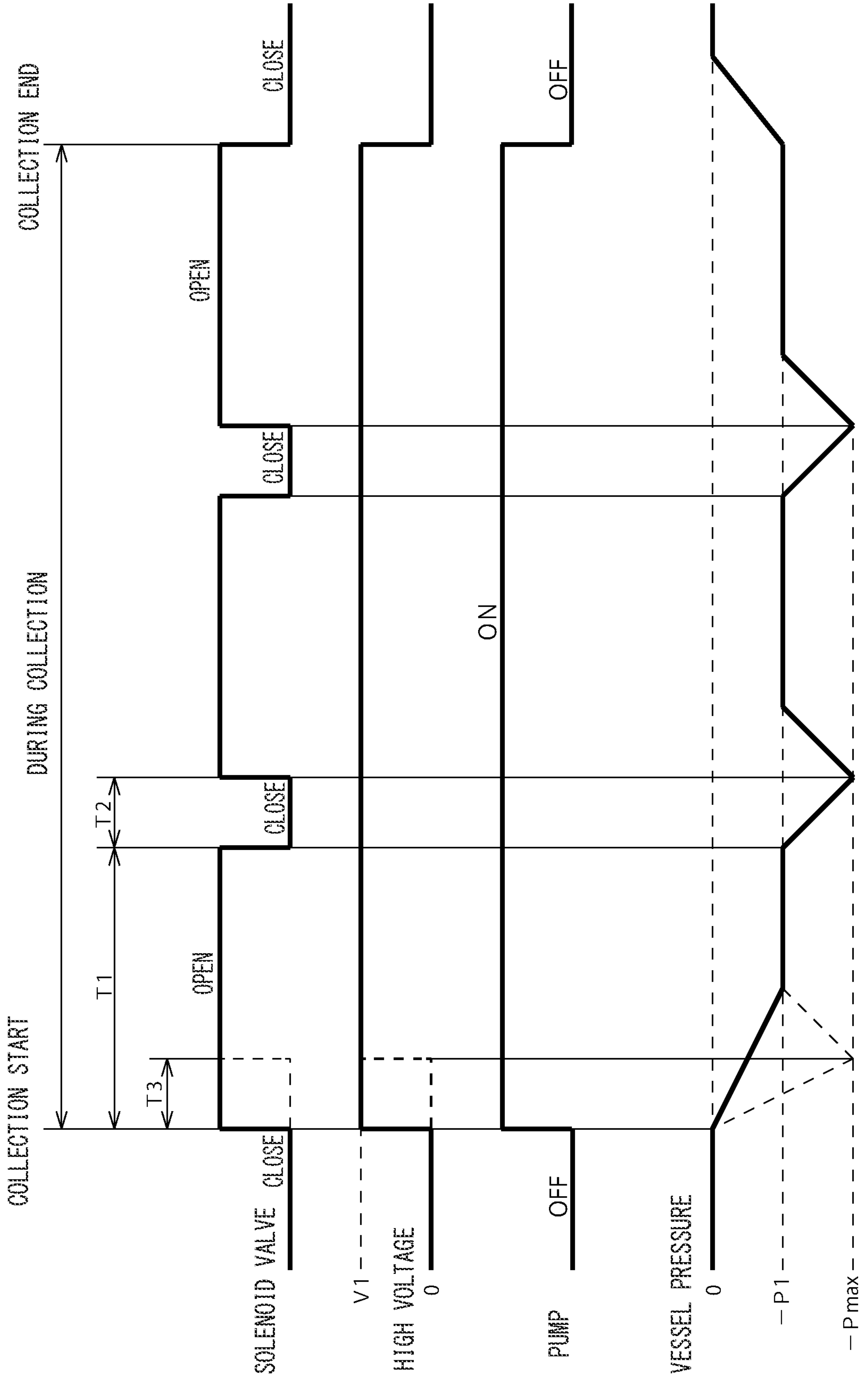
FIG. 11 is a time chart showing an operation of the particle collection device according to the embodiment of the present invention.

At this time, as shown by the dashed line in FIG. 11, at the time when the operation/stop switch 87 is turned on, after the pump 47 is driven, the timing of switching the solenoid valve 44 from the closed state to the opened state and the timing of applying the high voltage to the discharge electrode 15 may be delayed by a time T3. As a result, the internal pressure of the particle collection vessel 2 can be lowered (−Pmax), so that the velocity of the air flowing into the particle collection vessel 2 can be increased and the degree of mixing between the particles in the air and the liquid 11 can be increased.

Thereafter, based on a command from the CPU 81, the solenoid valve 44 is repeatedly switched from the closed state (T2) to the opened state (T1) at predetermined intervals. The closed interval T2 of the solenoid valve at this time is set shorter by the opened interval T1.

When the solenoid valve 44 is switched from the opened state to the closed state in this way, the internal pressure of the particle collection vessel 2 decreases, so that when the solenoid valve 44 is then switched from the closed state to the opened state, the air flows from the jetting port 68 of the jetting plate 62 toward the liquid surface vigorously, thus increasing the degree of mixing between the particles in the air and the liquid 11.

The clean air generated such that the particles are removed from the air and collected in the liquid 11 is discharged to the outside from the discharge port through the flow path 46 of the discharge equipment 5 from the outflow path 26 of the discharge part 16 of the electrode unit 12 and the discharge flow path 32 of the power supplying unit 3.

Then, when the operation/stop switch 87 is turned off, based on a command from the CPU 81, the solenoid valve 44 is switched to the closed state, the application of high voltage is stopped, and the pump 47 is stopped.

In the above description of the action of the particle collection devices 1 and 60, the action in the cases where the continuous operation is performed in the particle collection device 1 and the intermittent operation is performed in the particle collection device 60 is described, but for example, the intermittent operation may be performed by installing the solenoid valve 44 in the suction equipment 4 in the particle collection device 1, or the continuous operation may be performed in the particle collection device 60.

[Particle Collection Procedure] Next, the procedure for collecting the particles collected in the liquid 11 from the particle collection vessel 2 as described above will be described.

First, as shown in FIG. 3 and FIG. 7, the power supplying unit 3 is lifted manually or automatically to detach it from the electrode unit 12, the particle collection vessel 2 is detached from the particle collection devices 1 and 60, then the lid 9 (see FIG. 1) is attached to the particle collection vessel 2, and then the particle collection vessel 2 is stored as it is until the next processing is started.

In the next processing, the lid 9 is detached from the particle collection vessel 2, and the electrode unit 12 attached to the opening 8 of the vessel body 7 is detached. Since there is a possibility that virus adheres to the electrode unit 12, the electrode unit 12 is disposable and discarded. Then, using a pipette (a dropper) or the like through the opening 8, the liquid in the vessel body 7 in which the particles are collected is collected, and the collected liquid is measured in the next processing (for example, a PCR processing).

It should be noted that the above embodiment is a suitable specific example in the present invention and may be accompanied by various technically favorable limitations, but the technical scope of the present invention is not limited to these aspects unless otherwise stated.

INDUSTRIAL AVAILABILITY

The technique of the present invention can be suitably used for an air sampler and an airborne bacteria measuring device that collect microorganisms, bacteria and viruses in the air and measure the number of microorganisms, bacteria and viruses.

The invention claimed is:

1. A particle collection device comprising:
a particle collection vessel configured to charge particles in air and collect the particles; and
a power supplying unit detachably attached to the particle collection vessel, wherein
the particle collection vessel comprises:
a vessel body having an opening;
a suction part provided in the opening and having an inflow path configured such that the air is flowed from an outside into an inside of the vessel body through the inflow path;
a discharge part provided in the opening and having an outflow path configured such that the air is discharged from the inside to the outside of the vessel body through the outflow path;
a discharge electrode provided in the inside of the vessel body and configured such that a high voltage is applied to the discharge electrode; and
a medium storage part provided in the inside of the vessel body and capable of storing a medium for collecting the particles in the air charged by the discharge electrode,
the power supplying unit includes:
a suction flow path communicated with the inflow path of the particle collection vessel and configured such that the air is flowed into the inflow path through the suction flow path; and
a discharge flow path communicated with the outflow path of the particle collection vessel and configured such that the air discharged from the outflow path is flowed through the discharge flow path,
the particle collection vessel further comprises:
a power supplying contact part formed in the suction part of the particle collection vessel; and
a ground part configured to be in contact with the medium,
the power supplying unit further includes:
a power supplying member in contact with the power supplying contact part of the particle collection vessel and configured to apply the high voltage to the discharge electrode through the power supplying contact part; and
a ground member in contact with the ground part of the particle collection vessel and configured to be grounded,
the particle collection device further comprises:
an opening/closing valve provided in an upstream flow path of the suction flow path of the power supplying unit; and
a pump provided in a downstream flow path of the discharge flow path of the power supplying unit,
in operation, the pump is controlled to be operated continuously, and the opening/closing valve is controlled to be alternately opened and closed, and
in the operation, the opening/closing valve is controlled so that an opened time is longer than a closed time.

2. A particle collection method in which particles in air are collected using a particle collection device, wherein:
the particle collection device comprises:
a particle collection vessel configured to charge the particles in the air and collect the particles; and
a power supplying unit detachably attached to the particle collection vessel,
the particle collection vessel comprises:
a vessel body having an opening;
a suction part provided in the opening and having an inflow path configured such that the air is flowed from an outside into an inside of the vessel body through the inflow path;
a discharge part provided in the opening and having an outflow path configured such that the air is discharged from the inside to the outside of the vessel body through the outflow path;
a discharge electrode provided in the inside of the vessel body and configured such that a high voltage is applied to the discharge electrode; and
a medium storage part provided in the inside of the vessel body and capable of storing a medium for collecting the particles in the air charged by the discharge electrode,
the power supplying unit includes:
a suction flow path communicated with the inflow path of the particle collection vessel and configured such that the air is flowed into the inflow path through the suction flow path; and
a discharge flow path communicated with the outflow path of the particle collection vessel and configured such that the air discharged from the outflow path is flowed through the discharge flow path,
the particle collection vessel further comprises:
a power supplying contact part formed in the suction part of the particle collection vessel; and
a ground part configured to be in contact with the medium,
the power supplying unit further includes:
a power supplying member in contact with the power supplying contact part of the particle collection vessel and configured to apply the high voltage to the discharge electrode through the power supplying contact part; and
a ground member in contact with the ground part of the particle collection vessel and configured to be grounded,
the particle collection method comprises:
a medium supplying process in which the medium is supplied into the vessel body;
an air sucking process in which the air containing the particles is sucked into the vessel body after the medium supplying process;
a particle charging process in which the particles in the air sucked in the air sucking process are charged by applying the high voltage to the discharge electrode; and
a particle collecting process in which the particles charged in the particle charging process are collected in the medium supplied into the vessel body at the medium supplying process, and
the particles contain microorganisms, bacteria and viruses.

3. A particle collection vessel configured to charge and collect particles in air, the particle collection vessel comprising:
a vessel body having an opening; and
an electrode unit that is detachably provided in the opening of the vessel body, wherein
the electrode unit comprises:
a suction part including a cylindrical body inside which an inflow path is formed, the inflow path configured such that the air is flowed from an outside into an inside of the vessel body through the inflow path;

a supporting body supporting the cylindrical body; and a discharge part including an outflow path formed inside the supporting body and configured such that the air is discharged from the inside to the outside of the vessel body through the outflow path, the opening of the vessel body is formed at an upper portion facing a bottom portion of the vessel body, the inflow path and the outflow path penetrate the supporting body in an upper-and-lower direction, the cylindrical body includes one end opened to the outside of the vessel body and an other end opened to the inside of the vessel body, the electrode unit further comprises a discharge electrode provided at the other end of the cylindrical body and configured such that a high voltage is applied to the discharge electrode, and the vessel body comprises a medium storage part provided at the bottom portion of the vessel body and capable of storing a medium for collecting the particles in the air flowed into the inside of the vessel body and charged by the discharge electrode.

4. The particle collection vessel according to claim 3, wherein the medium is conductive, the electrode unit further comprises a ground part which is conductive and is configured to come into contact with the medium and to be grounded, the supporting body of the electrode unit is non-conductive and further supports the ground part, the cylindrical body supported by the supporting body is conductive, the one end of the cylindrical body opened to the outside of the vessel body is configured such that the high voltage is applied to the one end, the other end of the cylindrical body opened to the inside of the vessel body is configured to apply, to the discharge electrode, the high voltage applied to the one end, and a tip portion of the discharge electrode is provided at a position separated from the medium storage part capable of storing the medium by a first distance and protrudes from the other end of the cylindrical body toward the medium storage part.

5. The particle collection vessel according to claim 4, wherein the electrode unit further comprises a repulsion part provided at the other end of the cylindrical body and configured such that the high voltage is applied to the repulsion part by the other end of the cylindrical body, the repulsion part includes a flat plate having an opening at a position corresponding to a position of the cylindrical body, the repulsion part is arranged along the medium storage part and at a position separated from the medium storage part by a second distance so that a flow path is formed between the repulsion part and the medium storage part, the medium storage part capable of storing the medium, the flow path configured such that the air flowed from the opening of the flat plate into the inside of the vessel body is flowed through the flow path, and the second distance is set to be larger than the first distance.

6. The particle collection vessel according to claim 3, wherein the medium is a conductive liquid.

7. The particle collection vessel according to claim 6, wherein the cylindrical body is conductive, the medium storage part stores the conductive liquid, and the discharge electrode is provided at the other end of the conductive cylindrical body toward the conductive liquid.

8. The particle collection vessel according to claim 7, wherein an opening area of the other end of the conductive cylindrical body included in the suction part is set smaller than an opening area of said one end of the conductive cylindrical body.

9. The particle collection vessel according to claim 6, wherein the discharge electrode is formed of a wire electrode having a bundle of fibers.

10. The particle collection vessel according to claim 7, wherein the discharge electrode includes a plurality of discharge electrodes which are arranged at equal intervals along a circumferential direction of the conductive cylindrical body included in the suction part, and a tip portion of each of the plurality of discharge electrodes is provided so as to protrude toward a liquid surface of the conductive liquid from the suction part, and is arranged at a position separated from the liquid surface by a certain distance.

11. The particle collection vessel according to claim 7, further comprising:

a ground part extending toward the inside from the opening of the vessel body and coming into contact with the conductive liquid, wherein an outer circumference of the ground part is covered by a non-conductive insulating member.

12. The particle collection vessel according to claim 11, wherein a conductive biasing member is provided at a conductive liquid side end portion of the ground part.

13. The particle collection vessel according to claim 11, wherein the suction part includes a repulsion part, the repulsion part is provided along a liquid surface of the conductive liquid at a position separated from the liquid surface of the conductive liquid by a certain distance, and the repulsion part has a planar shape which is similar to the opening of the vessel body and smaller than the opening, and the repulsion part is supported by the other end of the conductive cylindrical body included in the suction part and by the ground part through an insulator.

14. The particle collection vessel according to claim 6, wherein a main component of the conductive liquid is water, and the conductive liquid is formed into a liquid film having a thickness of not more than 1 mm and contains a surfactant.

15. The particle collection vessel according to claim 6, wherein the conductive liquid contains an antioxidant, and the conductive liquid contains a deliquescent salt.

16. The particle collection vessel according to claim 3, wherein the bottom portion is formed flat, and an inner surface of the vessel body has a water-repellent property.

17. The particle collection vessel according to claim 3, wherein the vessel body is a vial.

18. The particle collection vessel according to claim 6, wherein the suction part includes the discharge electrode and a power supplying contact part, and the electrode unit is provided with the suction part, the discharge part and a ground part configured to be in contact with the conductive liquid.

19. The particle collection vessel according to claim 18, wherein an upper surface of the electrode unit is formed flat, and the suction part, the discharge part and the ground part do not protrude from the upper surface of the electrode unit.

20. The particle collection vessel according to claim 3, wherein the medium storage part stores the medium, and the medium is a gel, a jelly or a powder.

* * * * *